(12) United States Patent
Wilson et al.

(10) Patent No.: US 7,583,381 B2
(45) Date of Patent: Sep. 1, 2009

(54) MINIATURIZED FLUORESCENCE ANALYSIS SYSTEM

(75) Inventors: Denise M. Wilson, Lynnwood, WA (US); Andrew E. Moe, Shoreline, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/107,718

(22) Filed: Apr. 22, 2008

(65) Prior Publication Data

US 2008/0225290 A1 Sep. 18, 2008

Related U.S. Application Data

(62) Division of application No. 11/217,567, filed on Aug. 31, 2005, now abandoned.

(60) Provisional application No. 60/606,000, filed on Aug. 31, 2004.

(51) Int. Cl.
 *G01N 21/25* (2006.01)
(52) U.S. Cl. ..................................... 356/417
(58) Field of Classification Search ................. 356/317, 356/417; 250/458.1
 See application file for complete search history.

(56) References Cited

U.S. PATENT DOCUMENTS

| | | | |
|---|---|---|---|
| 5,445,795 A * | 8/1995 | Lancaster et al. | ........ 422/82.06 |
| 2002/0113213 A1 | 8/2002 | Amirkhanian et al. | |
| 2003/0016352 A1 | 1/2003 | Goldman et al. | |
| 2003/0030801 A1 | 2/2003 | Levenson et al. | |

OTHER PUBLICATIONS

Yotter, Rachel A. et al., "Sensor Technologies for Monitoring Metabolic Activity in Single Cells—Part I: Optical Methods," IEEE Sensors Journal, vol. 4, No. 4, Aug. 2004, pp. 395-411.

* cited by examiner

*Primary Examiner*—Kara E Geisel
(74) *Attorney, Agent, or Firm*—Blakely Sokoloff Taylor & Zafman, LLP (57) ABSTRACT

According to embodiments of the present invention, a fluorescence analysis system includes a light emitting diode to excite a fluorophor sample for analysis. The system includes an LED driver that pulses the LEDs in the array with currents in excess of maximum rated current at low duty cycles. One embodiment receives a first drive current at a light emitting diode (LED), emits excitation light having a first color and/or first wavelength band in response to the first drive current, receives a second drive current at the LED, and emits excitation light having a second color and/or second wavelength band in response to the second drive current, wherein at least one of the drive currents is greater than a nominal drive current for the LED.

23 Claims, 9 Drawing Sheets

FIG. 1

FIG. 2  Driver Circuit Schematic

FIG. 3  Typical Lifetime Characteristics

FIG. 4  Typical Lifetime Degradation

FIG. 5  Biological Analysis Results

FIG. 7A Optimization of GPFuv Fluorophore; The Optimized LED Excitation and Emission Spectrum as Compared to the Absorption Spectra of GFPuv.

FIG. 7B Optimization of GPFuv Fluorophore; A Non-optimized LED Configuration.

FIG. 7C  Optimization of GPFuv Fluorophore; A Single LED Configuration.

FIG. 8  Emission Spectrum

FIG. 9  LED Array Optimization

FIG. 10A  Results for Rhodamine Analysis

FIG. 10B  Results for Rhodamine Analysis

FIG. 11  Intensity Comparison (AM123)

MINIATURIZED FLUORESCENCE ANALYSIS SYSTEM

CROSS REFERENCE TO RELATED APPLICATIONS

This application is a Divisional of U.S. application Ser. No. 11/217,567, filed Aug. 31, 2005 now abandoned, which claims the benefit of U.S. Provisional Application No. 60/606,000, filed Aug. 31, 2004.

GOVERNMENT LICENSE RIGHTS

This invention was made with government support under grant number 1-P50-HG002360-01 awarded by the National Institutes of Health. The government has certain rights in the invention.

BACKGROUND

1. Field

Embodiments of the present invention relate to fluorescence analysis systems and in particular to light emitting diode (LED)-based fluorescence analysis systems.

2. Discussion of Related Art

Fluorescence is the emission of light by molecules which have absorbed light. The fluorescing characteristics of such molecules (called fluorophors) are useful in detecting and tagging various microbiological events. The emission signal is shifted to higher wavelengths (Stokes-Shift) in relation to the excitation signal because the energy of the fluorescing light emitted is less than the light absorbed by the fluorophor.

Fluorometers exploit the fluorescing property of fluorophor molecules in the analysis of biological samples. The simulation and optimization of a LED-based fluorometer should ideally maximize the efficiency with which light is converted to signal (emission) and minimize bleed-through excitation light to the output signal path. In other words, the overlap between excitation light source and emission spectra should be minimized so that once the excitation light is optically filtered from the output signal, maximum emission signal remains for measurement.

Conventional fluorescence analysis systems use a laser or a high power white light source (e.g. Xenon lamp) to excite fluorophors in the sample under analysis. LEDs (light emitting diodes) are of interest to replace conventional light sources to increase the portability (reduce power, size, and weight) of the analysis system and to improve the flexibility of excitation spectra available to the user with reduced optics overhead. Several approaches have been used in LED-based fluorescence analysis systems. LEDs are an attractive alternative to conventional white light sources used in fluorescence analysis because of reduced power of operation, fewer imaging artifacts, and increased flexibility in spectral control without the need for high overhead optics.

General purpose, commercially available portable systems, such as the Turner Biosystems [1][2] instruments have used single LEDs to excite fluorescing samples; these systems rely on the user to select the LED to match the fluorophor or vice versa. Many results in the literature rely on single or small arrays of LEDs, where excitation bands are chosen close to the excitation spectra of the fluorophor and the resulting emission spectrum is optically filtered to minimize interference from the excitation signal. Still other approaches excite a sample using different LEDs at different times and subsequent signal processing to improve the extraction of the emission signal from the combined output signal. Finally, a variety of waveguides have been constructed to minimize the transfer of excitation light along the output emission path at the expense of reduced sample volume.

The use of LEDs, however, is often limited by three primary factors: (a) the broadband output of an LED often interferes with the measurement of emission signal; (b) the power (intensity) of light generated by an LED (mWatts) is often small compared to white light source (Watts) counterparts; and (c) the excitation peaks of the LED are often not well matched to the absorption efficiency of the fluorophor under analysis. The use of LEDs, for this reason, has been largely limited to high concentration applications where emitted fluorescence is sufficiently high (and noise sufficiently low) that LED limitations do not restrict effective measurements of the sample under analysis. The spectral flexibility, modularity, low-cost, and low power consumption of LEDs, however, continue to make them attractive options for fluorescence analysis, however.

In many approaches using LEDs, the choice of LED (or LEDs) is usually not optimized prior to the collection of data by the fluorescence analysis system. Instead, the optics and signal processing are assigned the task of separating excitation components from the emission signal in the output path. In addition, many LED-based fluorescence analysis systems used in commercial and research efforts are general-purpose. This means that they are suited to a relatively wide selection of fluorophors and the biological applications to which they are applied.

SUMMARY OF EMBODIMENTS OF THE INVENTION

Embodiments of the present invention are directed to automated and modular optimization of fluorescence analysis system that may maximize signal extraction (SNR) from an excited fluorophor. In one embodiment, the system includes an array of light emitting diodes (LEDs) that emit excitation light. The excitation light may have a first color and/or wavelength (blue, blue-green, green, purple, or other suitable color/wavelength. The color and/or wavelength of the excitation light of one LED may be different than the color and/or wavelength of another excitation light of one LED.

The system also includes control electronics that apply drive currents to the LEDs. The drive currents cause the LEDs to emit the excitation light. The drive current to one LED may be different than the drive current to another LED. For some embodiments, the drive current is greater than nominal drive current, greater than rated maximum current for the LED, and in may range between twenty and two hundred milliamps. The control electronics may include an emitter follower circuit and/or source follower circuit to drive the LEDs.

The control electronics also may pulse the drive current to the LEDs with signals having low duty cycles. For example, in one embodiment, the control electronics may pulse the drive current to the LEDs with signals having duty cycles between one percent and twelve percent. In other embodiments, the control electronics may pulse the drive current to the LEDs with signals having duty cycles at or greater than twelve percent.

The system also includes optics to couple excitation light from the LEDs to a holder for the fluorophor. In one embodiment, an optical fiber bundle may be coupled to each individual LED so that each LED has its own optical fiber bundle associated with it. The optical fiber bundles may be bundled together so that the excitation light from the LEDs may be aggregated into a single light beam that has a substantially uniform intensity profile and/or a substantially uniform wavelength distribution. The bundle of bundles couples the single light beam to the fluorophor holder. In one embodiment, the optical fiber bundles are bundled together in a random manner.

For some embodiments, the system may include a beam splitter to split off a small portion of the single light beam and to direct the small portion to circuitry to measure the intensity of the small portion of the single light beam as a function of the color and/or wavelength. The circuitry may adjust drive current to one or more LEDs in response to the measured intensity of the small portion of the single light beam. The circuitry may be a spectrophotometer.

For other embodiments, one or more PIN diode may be coupled to one or more LEDs, respectively, to detect the excitation light emitted from the LED. There may be circuitry to adjust one or more drive currents in response to the detected excitation light.

When the excitation light impinges on a fluorophor placed in the fluorophor holder, the fluorophor may emit light that in response to the excitation light. The emitted light may have a color and/or wavelength that is different than the color and/or wavelength of the excitation light. In one embodiment, the fluorophor holder may be a cuvette.

The system also includes a photodetector to detect light emitted from the fluorophor. The photodetector may a photomultiplier tube, an avalanche photodiode, photodiode, phototransistor, and/or a charge-coupled device (CCD).

The system also includes optical fiber to couple the light emitted from the fluorophor to the photodetector.

For some embodiments, the system may be used to select a configuration for the LED array. The system may determine at least two possible permutations of LEDs for the LED array and for each permutation determine a total excitation light that is to be emitted from the LED array, determine an amount of excitation light that is to reach the fluorophor based on the total excitation light emitted from the LED array, determine an amount of light that is to be transmitted through the fluorophor based on the amount of excitation light that is to reach the fluorophor, based on an amount of attenuation in an emission path to a photodetector from the fluorophor in the fluorescence analysis system, and based on filtering of the light that is to be transmitted through the fluorophor, determine an amount of light that is to be emitted by the fluorophor based on the amount of excitation light that is to reach the fluorophor and based on the amount of light that is to be transmitted through the fluorophor, determine an amount of light that is to reach the photodetector based on the amount of light that is to be emitted by the fluorophor, and determine a leakage penalty for the fluorescence analysis system based on the amount of light that is to be transmitted through the fluorophor and based on the amount of light that is to reach the photodetector. The system then compares the leakage penalties for each permutation of LEDs in the LED array and ranks the permutations of LEDs in the LED array based on the comparison of their respective leakage penalties.

In one embodiment, the system may receive from a user information associated with a type of LEDs to be selected from a database, information associated with a number of LEDs to be placed in the LED array, information associated with the fluorophor of interest, information associated with at least one undesirable fluorophor, information associated with a minimum concentration detection capability for the fluorophor of interest, and/or information associated with a time frame within which to perform fluorescence analysis on the fluorophor of interest.

The system may, for each permutation of LEDs in the LED array, determine optical power and/or spectral shape of an aggregate output of the LED array, receive information associated with spectral characteristics of the photodetector, calculate output current and/or output voltage of the photodetector based on the information associated with the spectral characteristics of the photodetector, determine a drive current for each LED in the LED array based on the leakage penalty, determine a duty cycle for the drive current based on the leakage penalty, and/or determine a duty cycle in the range of one percent to twelve percent for the drive current based on the leakage penalty.

For some embodiments, optimizing software may be used to perform the above-described method. In these embodiments, the software may be a machine-readable medium having data to cause a machine to select a configuration for the LED array.

As will be described below, the optimization software takes into account a variety of factors of practical fluorescence analysis including optics, photodetector properties, attenuation in the sample itself, and leakage of the excitation signal to the output signal path. While most fluorometer systems use a single light source such as a Xenon or Mercury lamp, in embodiments of the present invention the optimization software relies on a combination of several LEDs in an array driven at various nominal and overdrive currents. Overdriving the LEDs enables spectral shifts from nominal peak excitation wavelengths that increase the flexibility and intensity of spectra identified by optimization software. Given a fluorophor, environmental conditions, and optical path constraints, the optimization software may generate the best possible combination of LEDs to excite the sample and maximize the emission signal collected in the output path.

BRIEF DESCRIPTION OF THE DRAWINGS

In the drawings, like reference numbers generally indicate identical, functionally similar, and/or structurally equivalent elements. The drawing in which an element first appears is indicated by the leftmost digit(s) in the reference number, in which:

FIG. 7, including 7(a), 7(b), and 7(c) is a graphical representation illustrating results generated by the process depicted in FIG. 6 for evaluating GFPuv according to an embodiment of the present invention;

DETAILED DESCRIPTION OF THE ILLUSTRATED EMBODIMENTS

Figure 1:
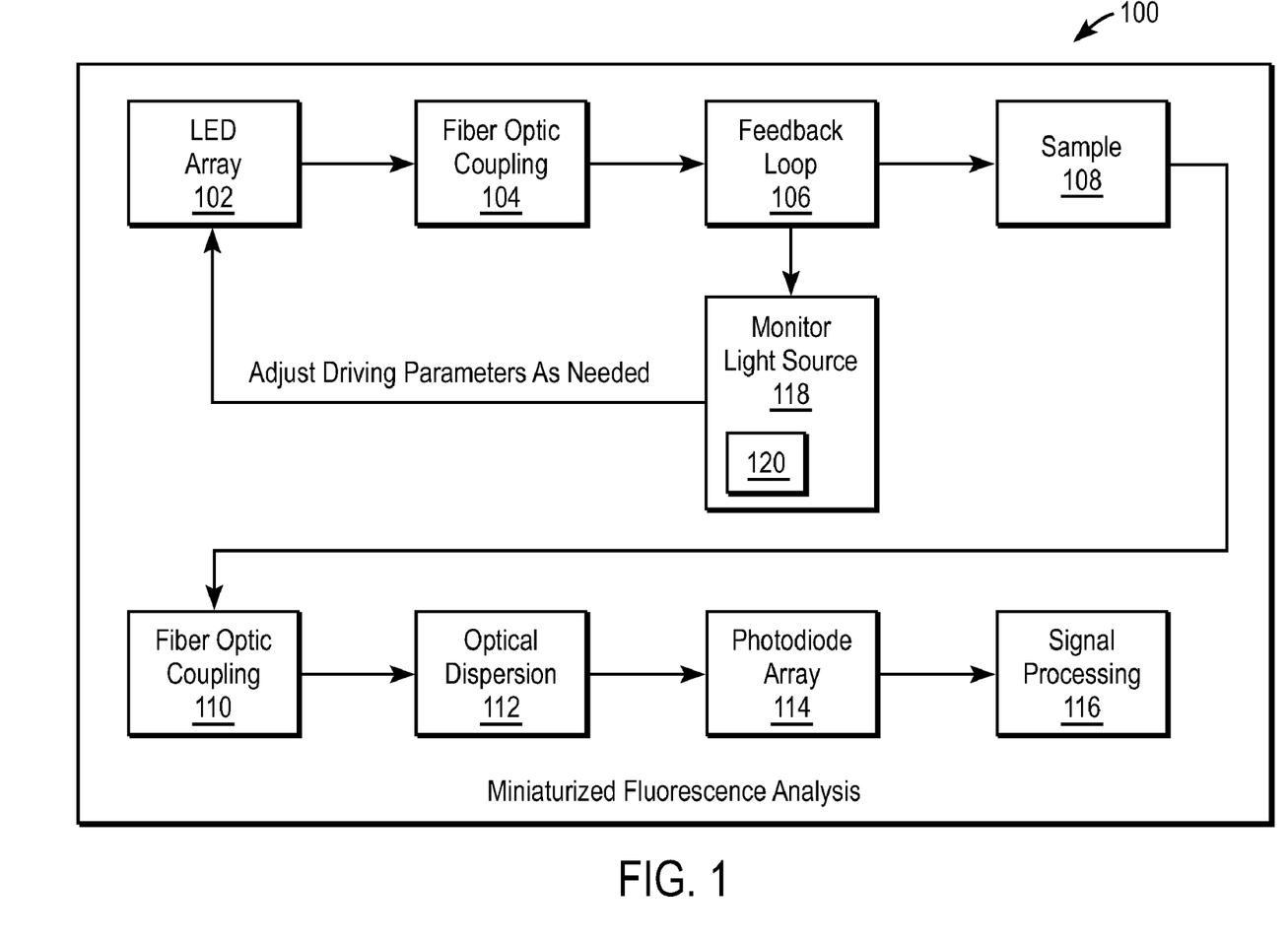
FIG. 1 is a high-level block diagram illustrating a miniaturized fluorescence analysis system according to an embodiment of the present invention.

FIG. 1 is a high-level block diagram illustrating a miniaturized fluorescence analysis system 100 according to an embodiment of the present invention, in which an LED array 102 is coupled to fiber optic coupling 104. The fiber optic coupling 104 is optionally coupled to a beam splitter 106, which is part of a feed back loop. The example fiber optic coupling 104 may be coupled to a sample 108 (e.g., fluorophor) without the feed back loop. The sample 108 is coupled to fiber optic coupling 110, which is optionally coupled to one or more optical dispersion devices 112. The fiber optic coupling 110 may be coupled to a photodiode array 114 without the optical dispersion devices 112. The photodetector 114 (shown as a photodiode array) is coupled to a signal processing module 116. A monitor light source module 118 is coupled in the feed back loop between the beam splitter 106 and the LED array 102. The illustrated module 118 includes an LED driver 120.

LEDs are traditionally less stable than their white light source counterparts. In the system 100, the real-time feedback loop monitors the LED array 102 output and adjusts the LED array 102 drive currents and output powers to maintain a stable signal into the fluorophor sample 108. The output light passes from the LED array 102 through the randomizing fiber optic coupling 104, and into the beam splitter 106, where most of the light travels to the sample 108 (for exciting the fluorophor or other luminescing sample). A small percentage of the light may be fed back to a spectrophotometer in the monitor light source module 118 where it is analyzed for power and spectral properties, for example. The spectrophotometer sends power and spectral information to a microcontroller in the monitor light source module 118, which is then used to adjust the LED array 102 output properties through the LED driver 120.

For some embodiments, the LED array 102 is a highly flexible, modular LED array having several LEDs of different types (e.g., purple, blue, blue-green, and green) operating under several different possible drive currents (e.g., 5 and 20 mA are nominal operating conditions and 50, 100, and 150 mA are overdrive currents that not only increase the intensity of LED output but also produce fine shifts (in wavelength) of the spectral properties of the LED). In one embodiment, using type and drive current as variables, the 5-element LED array can produce a maximum of 3.2 million possible aggregate spectra.

The LED driver 120 is designed to be a dynamic, feedback driven light source suitable for use in fluorescence analysis systems. It is designed as a solution to common drawbacks of conventional fluorescence light sources (large cost, power, and size) and resolves issues associated with using LEDs as light sources for fluorescence analysis. (low intensity, stability, and lifetime, poor spectral control). An obstacle to using LEDs as a light source for fluorescence analysis is the small light intensity produced as compared to a conventional light source (Xenon lamp). The LED driver 120 solves this problem by overdriving the LEDs in the LED array 102 with very high currents, up to and beyond ten times the rated maximum current for the LED (20 mA DC), for example. Normal operation at these currents using DC may destroy the LED, but the LED driver 120 has solved this problem by pulsing the LEDs in the LED array 102 at these high currents for very short periods of time, in the range of 1-12% duty cycle, for example. Light intensity out of an LED is proportional to the input current, therefore each pulse of the LED may produce ten times the normal light intensity produced under manufacturer's operation specifications. By pulsing the LEDs in this way, lifetime degradation due to high currents may be reduced.

An additional side-effect of pulsing an LED at a high current with a low duty cycle is a shift in the spectral output of the LED. As mentioned above, one of the key problems encountered when using LEDs as a light source for fluorescence analysis is poor spectral control of the LED light output. Limited output spectra are available because LEDs are available only in discrete fixed wavelengths, as well as a few broadband LEDs. Creating a broadband light source from LEDs is difficult because of the extreme difference between types of LEDs. Some colors have higher intensities than others, "white light" LEDs are predominantly blue, and there can be both spectral and intensity differences between two LEDs of the same color and type.

These inconsistencies are solved with the LED driver 120, which adjusts intensity variations using driving current. In this manner, the spectral shift side-effect mentioned above, which is usually regarded as an inhibitor to using LEDs as light sources, is exploited to adjust the spectral output of the LEDs to match the light source needs of the application. By driving an array of LEDs, aggregated into a single light source, the LED driver 120 creates a tunable light source.

Figure 2:
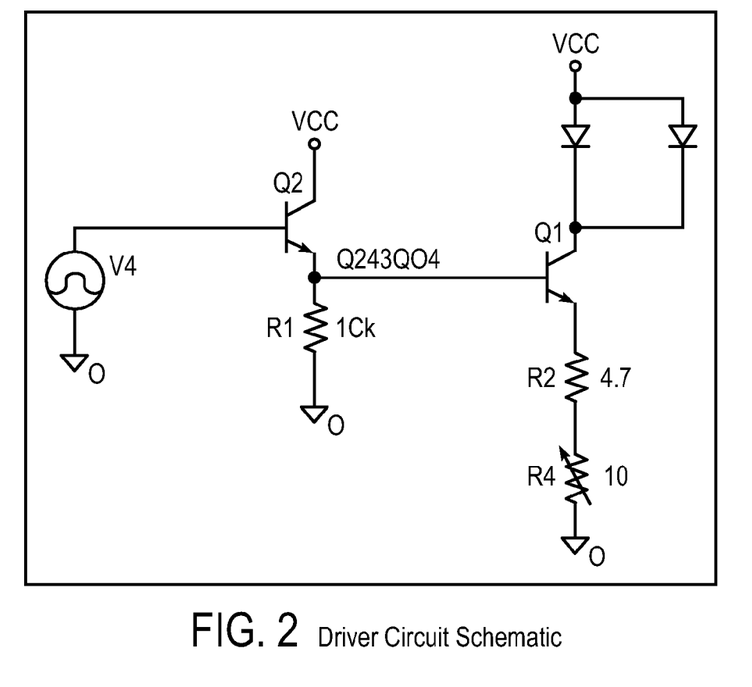
FIG. 2 is a schematic diagram illustrating the LED driver depicted in FIG. 1 according to an embodiment of the present invention.

In one embodiment, the LED driver 120 may be a printed circuit board (PCB) having four high current driver circuits as shown in FIG. 2, which is a schematic diagram of the LED driver 120 according to an embodiment of the present invention. The illustrated LED driver 120 may be capable of controlling a pair of LEDs at user adjustable duty cycles between one percent and twelve percent and at current levels between ten milliamps and two hundred milliamps. In the LED driver 120, an emitter-follower (or source follower if using CMOS technology) supplies high current to the driving transistor Q1. A crystal oscillator (not shown) and a series of counters (not shown) may supply the low duty cycle driving signal to the LED drivers 120.

Figure 3:
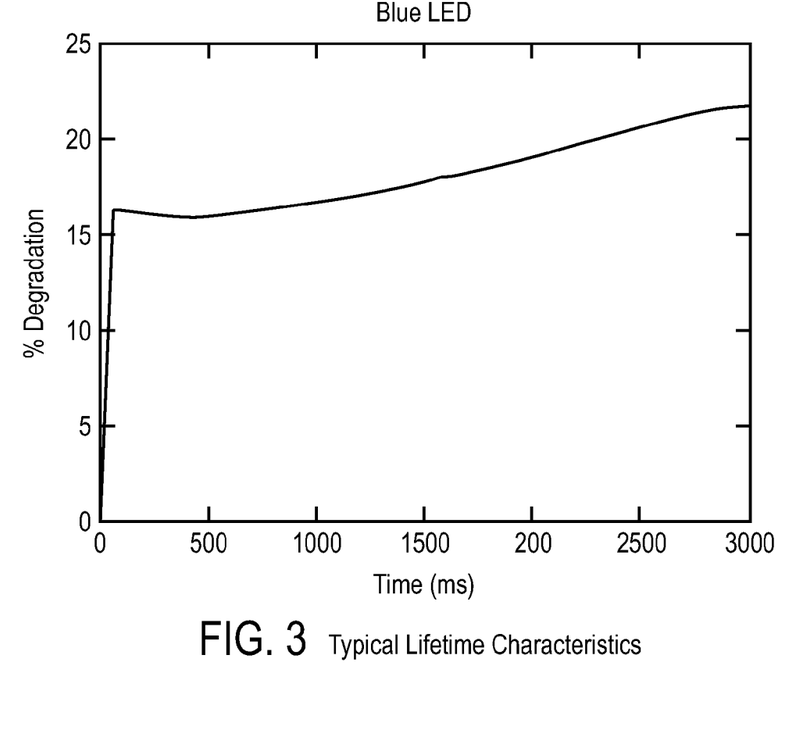
FIG. 3 is graphical representation illustrating experimental measurements of various commercially available LEDs across time and drive current to characterize their effective lifetime according to an embodiment of the present invention.

Various commercially available LEDs (blue, blue-green, purple, green) have been experimentally measured across time and drive current to characterize their effective lifetime. An example of the characterization results is shown in FIG. 3. The higher the drive current, the shorter the lifetime of the LED. However, lifetime degradation can be circumvented, for fluorescence analysis applications, by reducing the duty cycle of the LED, so that they are activated long enough to excite fluorescence, but not so long as to prematurely degrade the useful lifetime of the LED.

Figure 4:
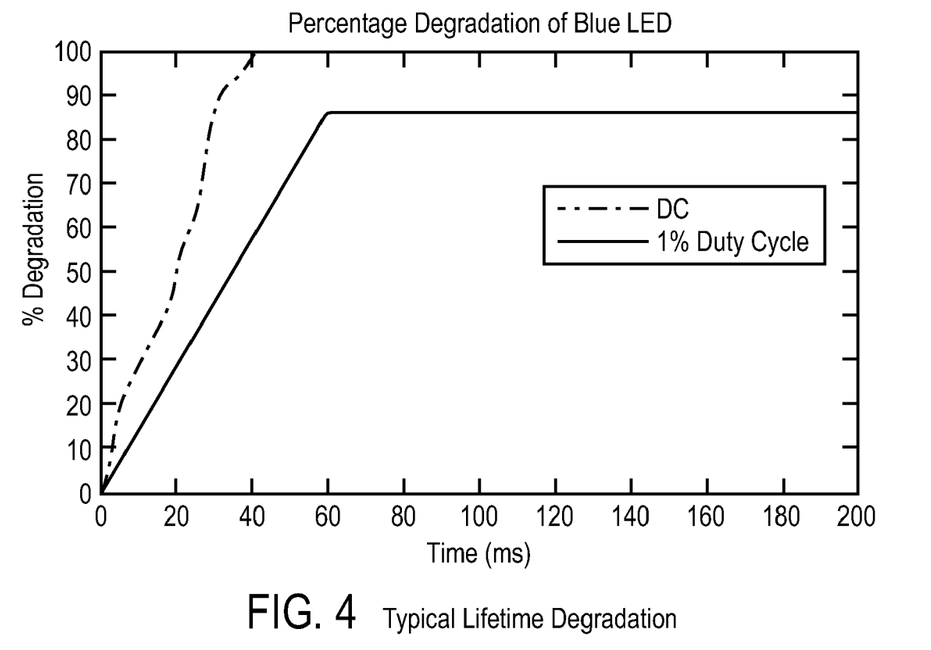
FIG. 4 is graphical representation illustrating experimental demonstration of increased lifetime of the reduced duty cycle according to an embodiment of the present invention.

Experimental demonstration of increased lifetime of the reduced duty cycle approach is shown in FIG. 4 for DC operation (100% duty cycle) and low (1%) duty cycle operation. Lifetime of the blue LED shown in these results improves by an average of 30% using the LED driver 120.

Figure 5:
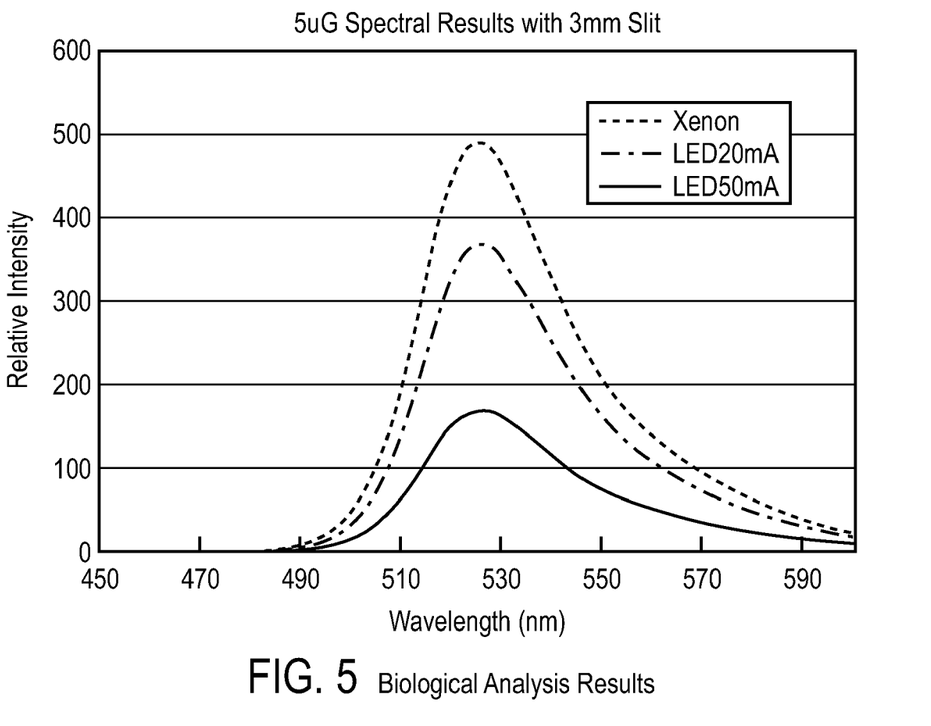
FIG. 5 is a graphical representation illustrating an example of the effectiveness of LED as compared to Xenon excitation according to an embodiment of the present invention.

Using high drive currents, it is possible to achieve the power levels of conventional light sources in practical biological analysis experiments. An example of the effectiveness of LED as compared to Xenon excitation is shown in FIG. 5. This experiment captures the fluorescence of AM1 bacteria tagged with UV-GFP fluorophor. An array of 7 purple LEDs operating at 50 mA currents are used to excite the UV-GFP tagged bacteria at comparable levels to the Xenon light source in a standard Shimadzu RF3401 fluorometer. Standard growth studies are typically performed over a 24 hour period with data collection occurring every 3 hours. These experiment lengths cannot be accommodated with LEDs at high currents, using DC operation, but fall well within the limits of LEDs operating at the reduced duty cycles controlled by the LED driver module described herein. These types of electronic interface and control modules are essential to the effective use of LEDs and LED arrays in low-level fluorescence analysis.

The fiber optic coupling 104 includes an optical fiber bundle coupled to each individual LED so that each LED. The optical fiber bundles are bundled together in a random manner to aggregate the excitation light into a single light beam. Without the random fiber optic coupling 104 the output of the LED array 102 might be a series of discrete spots that may excite the sample 108 in an unpredictable and unstable manner.

The sample 108 may be held in a standard, commercially available cuvette holder, but may be coupled within the system 100 via the fiber optic coupling 104 and the fiber optic coupling 110 rather than traditional optical components. The fiber optic couplings 104 and 110 may be any suitable single mode or multimode optical fibers. The fiber optic couplings 104 and 110 also reduce or eliminate the need for periodic or unpredictable realignment of optics.

The photodetector 114, although shown as photodiodes, may be any conventional photomultiplier tubes, avalanche photodiodes, low power photodiodes, phototransistors, charge-coupled devices that are compatible with portable, small footprint systems. Alternative photodetection schemes may be enabled by the reduced optical losses in the system 100 incurred by the use of fiber optic couplings 104 and 110 rather than discrete optics an the absence of slits required for white light sources, which also decrease optical throughput.

The LED configuration may be optimized using a design simulation program that accounts for LED output characteristics, optical filtering and losses, photodetector properties, sample characteristics, sample attenuation and other factors in seeking the "best" LED configuration in terms of overlap between the emission and excitation spectra, total emission intensity (SNR), or both.

Figure 6A:
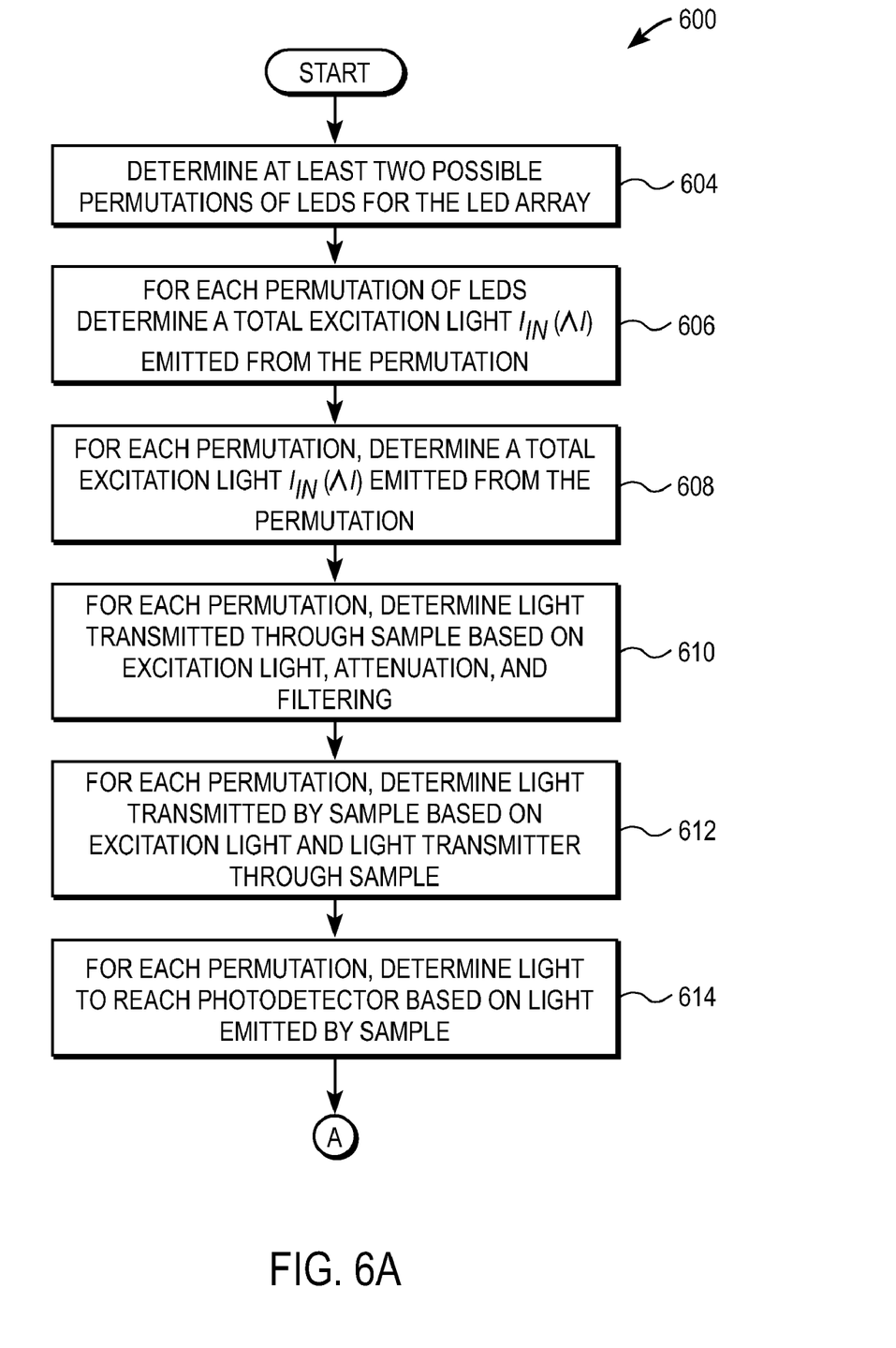
FIGS. 6A and 6B illustrate a flowchart of operation of the system depicted in FIG. 1 according to an embodiment of the present invention.
Figure 6B:
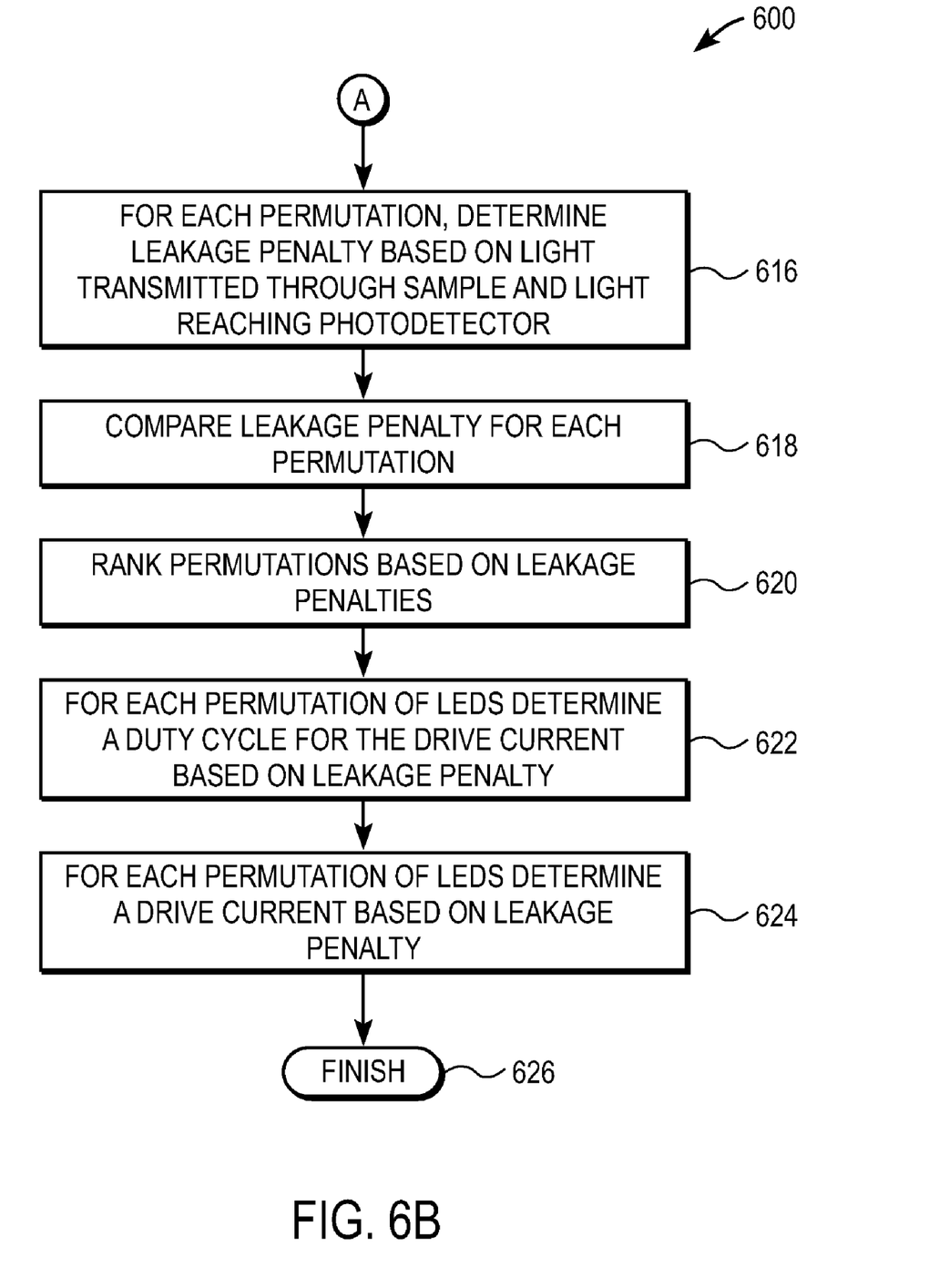

FIG. 6 is a flowchart of a process 600 illustrating operation of the system 100 according to an embodiment of the present invention. The process 600 may be implemented using hardware, software, or a combination thereof. In implementations using software, the software may be stored on a machine-accessible medium. In a block 602 the process 600 begins and control passes to a block 604.

In a block 604, the process 600 determines at least two possible permutations of LEDs for the LED array 102.

In a block 606, for each permutation of LEDs in the LED array, the process 600 determines a total excitation light $I_{IN}(\lambda i)$ that is to be emitted from the permutation of LEDs to be placed in the LED array 102.

In a block 608, the process 600 determines an amount of excitation light that is to reach the fluorophor sample 108 based on the total excitation light emitted from the permutation of LEDs. At a particular wavelength, $\lambda i$, the light that reaches the sample 108 may be expressed as $I_S(\lambda i)$:

$$I_S(\lambda_i) = I_{IN}(\lambda_i) \times A_L \times F_L(\lambda_i) \tag{1}$$

where $I_{IN}(\lambda i)$ is the total excitation light (Watts) impinging on the sample at wavelength $\lambda i$, that is attenuated by the optical loss in the excitation path $A_L$ and by $F_L(\lambda i)$, the transmissivity of filter in the excitation path.

In a block 610, the process 600 determines an amount of light that is to be transmitted through the fluorophor sample 108 based on the amount of excitation light that is to reach the fluorophor sample 108, the amount of attenuation in the emission path to the photodetector array 114 from the fluorophor sample 108, and based on filtering of the light that is to be transmitted through the fluorophor sample 108. The light that is transmitted through the sample, rather than absorbed by the fluorophor can be expressed, according to Beer's Law, in terms of the extinction coefficient $\epsilon(\lambda i)$ to obtain $I_{L\_max}(\lambda i)$:

$$I_{L\_max}(\lambda_i) = I_S(\lambda_i) \times (10^{-\epsilon(\lambda_i)cL}) \tag{2}$$

where $\epsilon(\lambda i)$ is the extinction coefficient (liters/cm*mole) at wavelength $\lambda i$ and is given by the excitation spectrum for the fluorophor sample 108, c is the concentration of fluorophor sample 108 in the sample (moles per liter); and L is the fluorophor sample 108 path length (cm).

The transmitted light may then be attenuated by optical losses ($A_E$) and filtered ($F_E(\lambda i)$) in the emission path to obtain $I_L(\lambda i)$:

$$I_L(\lambda_i) = I_{L\_max}(\lambda_i) \times A_S \times A_E \times F_E(\lambda_i) \tag{3}$$

The factor $A_S$ accounts for scattering and other losses between the sample and the output optical path. The light that is not transmitted through the fluorophor sample 108 is absorbed.

In a block 612, the process 600 determines an amount of light that is to be emitted by the fluorophor sample 108 based on the amount of excitation light that is to reach the fluorophor sample 108 and the amount of light that is to be transmitted through the fluorophor sample 108. Some of this absorbed light is then emitted as fluorescence $I_E$:

$$I_E = (I_S - I_{L\_max}) \times Q \tag{4}$$

where the factor Q represent fluorescence efficiency (quantum yield), and is a function of such variables as pH, temperature, and heavy metal ion concentration; $I_S$ and $I_L$max represent the total light reaching the sample 108 and transmitted light, respectively, integrated across all wavelengths $\lambda i$. The total emitted light $I_E$ is redistributed across wavelength $\lambda i$ according to the emission spectrum of the fluorophor sample 108 (available from the manufacturer).

In a block 614, the process 600 determines an amount of light that is to reach the photodetector array 114 based on the amount of light that is to be emitted by the fluorophor sample 108. The fluorescence signal that reaches the photodetector array 114 at the end of the optical path is then given by $I_E'$:

$$I_E'(\lambda_i) = I_E(\lambda_i) \times A_E \times F_E(\lambda_i) \tag{5}$$

In a block 616, the process 600 determines a leakage penalty for the fluorescence analysis system 100 based on the amount of light that is to be transmitted through the fluorophor sample 108 and based on the amount of light that is to reach the photodetector array 114. In order to optimize fluorescence emission, a performance metric P is defined as follows:

$$P(\lambda_i) = \frac{I_L(\lambda_i)}{I_L(\lambda_i) + I_E'(\lambda_i)} \tag{6}$$

This dimensionless parameter is a measure of how much leakage from the excitation process affects the emission signal and is analogous to the reciprocal of SNR (signal to noise ratio) in electronic circuits. This penalty P can then be integrated across the visible light spectrum:

$$P = \int_{\lambda_{min}}^{\lambda_{max}} P(\lambda_i) d\lambda \qquad (7)$$

It is this metric that is optimized (reduced and/or minimized) by the process 600. Ultimately, this metric includes effects of significant interferents as well as bleed-through from the excitation signal. These factors that attenuate the signal in the excitation path, sample, emission path, and filtering properties of the excitation and emission paths can be adjusted by the user. The process 600 uses these parameters in combination with the targeted fluorophor and sample 108 characteristics to generate a ranked series of LED configurations that reduce the penalty metric P.

Figure 7A:
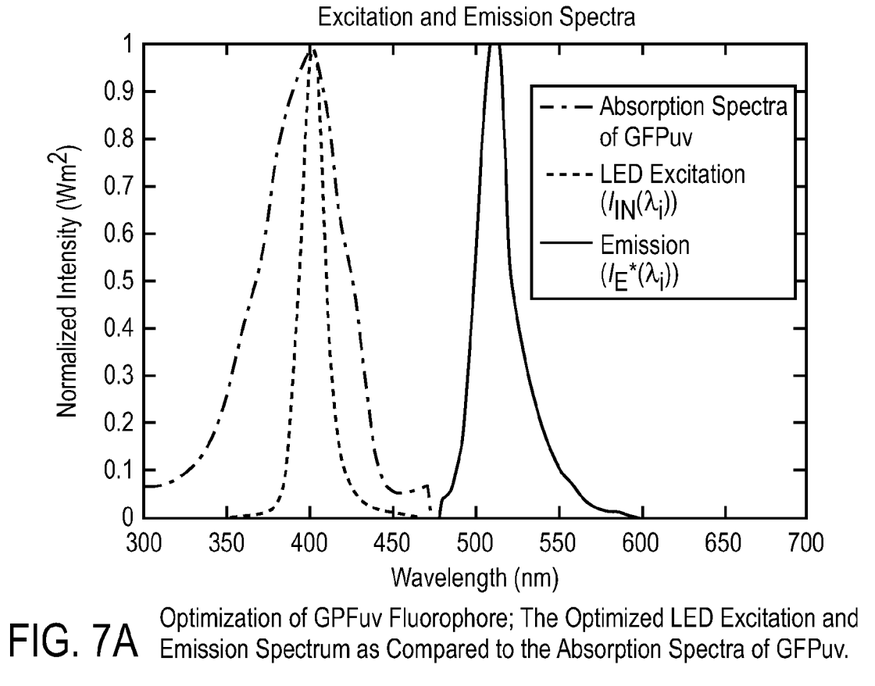
Figure 7B:
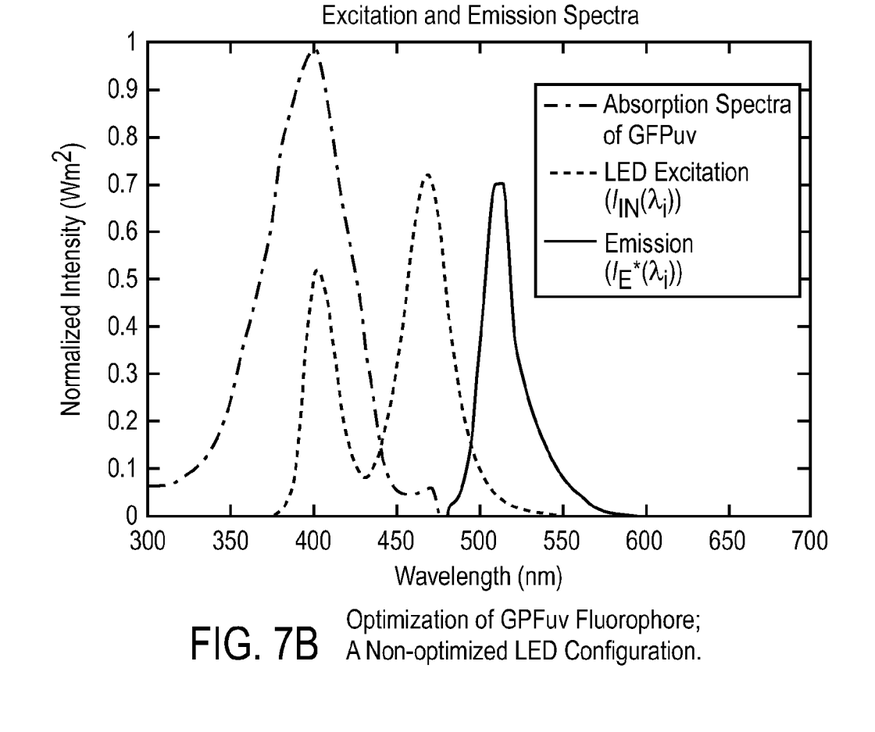

In a block 618, the process 600 compares the leakage penalties for each permutation of LEDs in the LED array 102. Results generated by the process 600 for evaluating GFPuv are shown in FIG. 7 for (a) an optimized excitation spectrum, and (b) a non-optimized configuration.

In a block 620, the process 600 ranks the permutations of LEDs in the LED array 102 based on the comparison of their respective leakage penalties.

In a block 622, for each permutation of the LEDs in the LED array 102 the process 600 determines a duty cycle in the range of one percent to twelve percent for the drive current based on the leakage penalty.

In a block 624, for each permutation of the LEDs in the LED array 102 the process 600 determines a drive current for each LED in the LED array 102 based on the leakage penalty. In one embodiment, the drive current is significantly in excess of a rated maximum current for the at least one LED in the LED array 102. In a process 626, the process 600 finishes.

In one embodiment, the process 600 has been optimized in a representative application for the excitation of GFPuv and has been compared to a single LED light source. The simulation parameters are chosen for proof-of-concept only. Although most fluorescence systems use some sort of optical filtering to reduce the interference of excitation with emission signal, it is possible, within the flexibility and modularity of the process 600 that some applications (that measure spectra rather than total intensity) will not require optical filtering and hence will not suffer from the optical losses associated with such filtering. Interfering effects such as autofluorescence and Raman scattering can be implemented into the current the process 600 and may be used to optimize even more accurately the system design to the needs of the targeted application.

Currently, the system 100 has a database consisting of several LEDS (blue, blue-green, green and purple) operating at drive currents from 1 mA to 100 mA (corresponding to spectral shifts from 0 nm to 10 nm from the peak wavelength at nominal operation). The penalty metric described in the previous section is minimized to determine the optimal combination of LEDs for each application.

The process 600 rates a range of optimizing LED combinations by comparing penalty calculations. The penalty for the best configuration is calculated at 0.159, compared to the less efficient non-optimized configuration at 0.365. The emission spectra resulting from the excitation by the closest matching single LED is compared to the GFPuv absorption spectra in FIG. 7(c). From the data plotted in these figures, it can be shown that the optimized spectrum from the LED array 102 reduces the excitation signal leakage into the output path and improves the emission signal that can be collected for interpretation. Performance improvements over single LED excitation show a 70.1% increase in collected emission signal for GFPuv fluorophors. The best non-optimized and single LED configurations are shown in Table 1 below.

TABLE 1

| Configurations for GFPuv fluorophors | | |
| --- | --- | --- |
| Configuration | LEDs | Current |
| Best | 1 purple | 10 mA |
| | 2 purple | 20 mA |
| | 2 purple | 50 mA |
| Non-optimized | 1 blue | 10 mA |
| | 1 blue | 100 mA |
| | 2 purple | 20 mA |
| | 1 purple | 10 mA |
| Single LED | 1 purple | 50 mA |

Figure 7C:
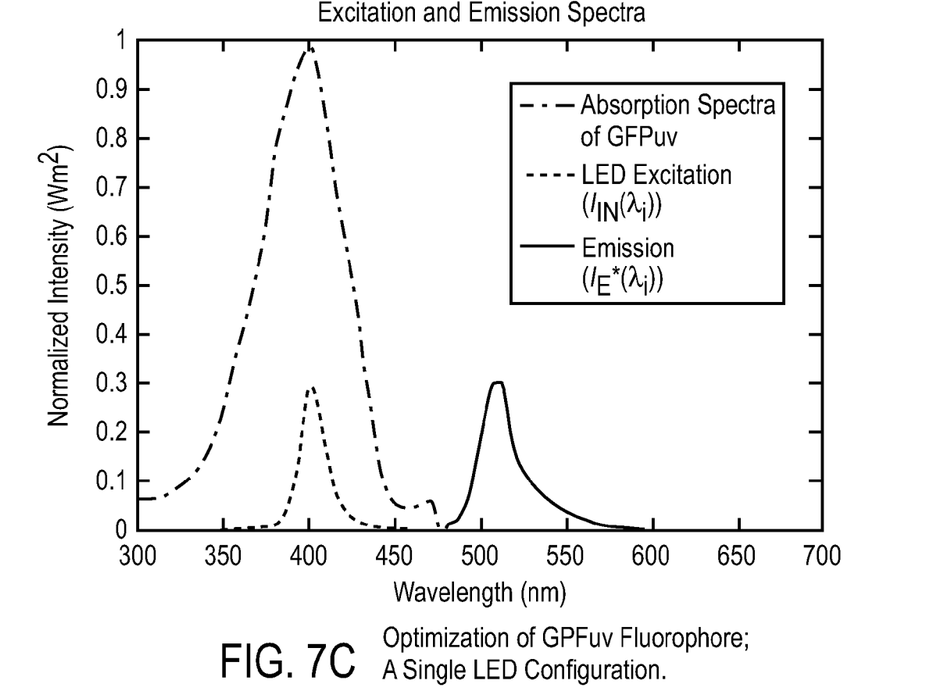
Figure 8:
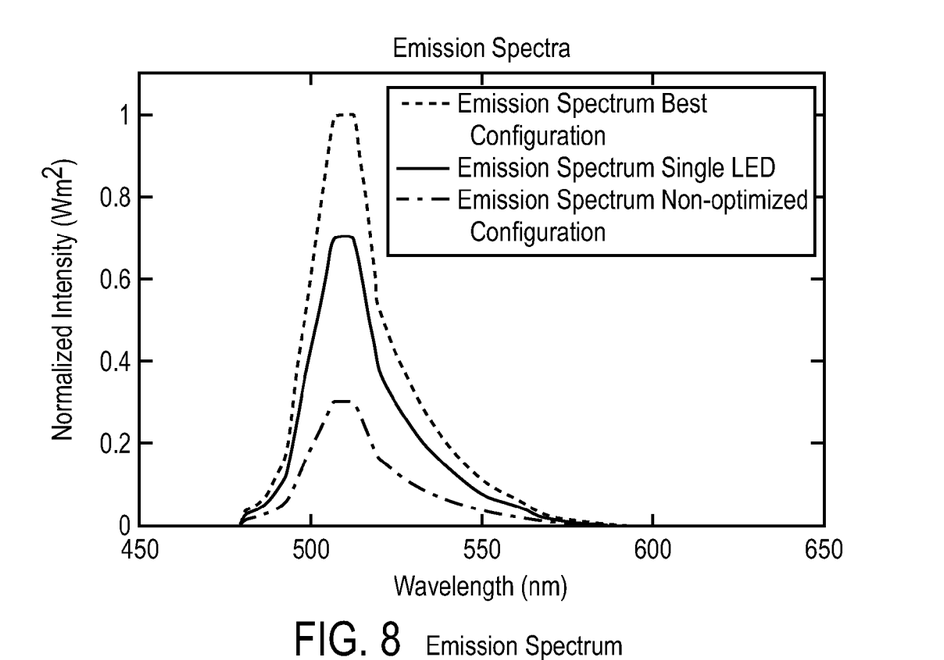
FIG. 8 is a graphical representation of an emission spectrum according to an embodiment of the present invention.

FIG. 8 compares all three emission spectrum from FIG. 7 to demonstrate the analysis that is achieved by the process 600 in determining the optimal configuration of LEDs in the LED array 102. A 70.4% improvement in the excitation signal over the single LED is achieved by the best configuration. These improvements support the use of design optimization of process 600 prior to the experimentation and fluorescent signal analysis.

In an alternative embodiment, the optimal configuration provided by the process 600 may be implemented in a 5-element LED array 102 with the LED driver 120 to reduce the duty cycle to the LEDs (for improving reliability and lifetime of the over driven LEDs). The outputs of the LEDs may then be coupled into a randomized fiber optic bundle to provide a uniform input to the sample under analysis (eliminating the imaging artifacts common to many white light sources). In this experimental embodiment, the LED array 102 and fiber optic bundle 104 may be coupled into a Shimadzu RF3401 fluorometer and the outputs measured in a manner comparable to when a Xenon source is used for sample 108 excitation. In one embodiment, the LED configuration is optimized for three representative applications as follows: (1) a theoretical desired spectral output; (2) the excitation of Rhodamine dye; and (3) the excitation of bacteria; GFPuv is cloned into Methylobacterium extorquens AM123, such that when suspended in liquid media, the fluorescent intensity of the cells is indicative of the cell concentration.

Figure 9:
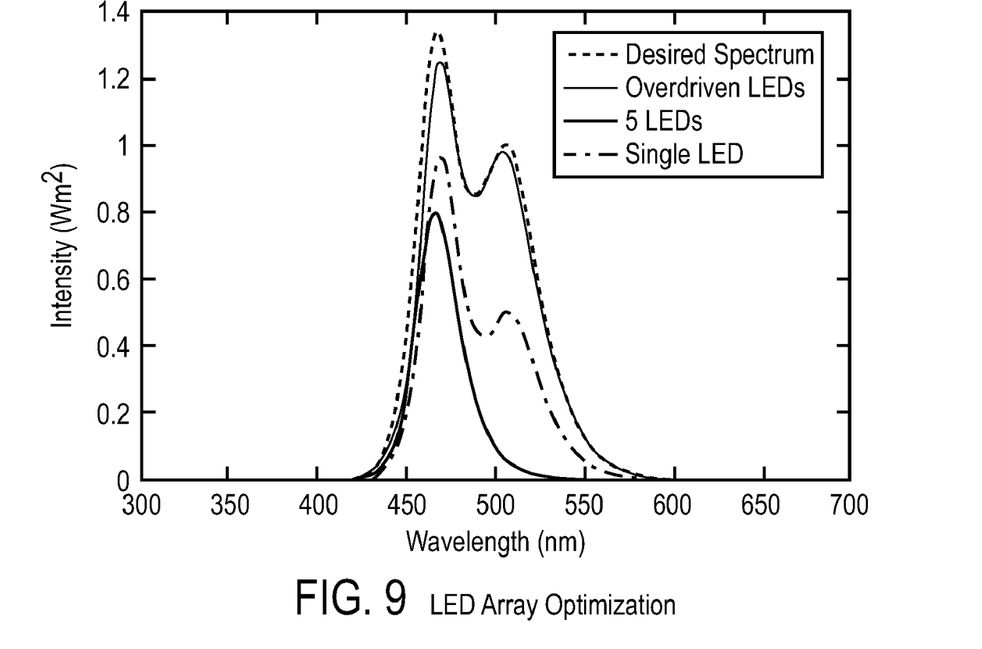
FIG. 9 is a graphical representation of the results of LED array optimization according to an embodiment of the present invention.

To demonstrate the capability of this LED array 102 over its closest alternatives, a desired spectrum is arbitrarily generated as shown in FIG. 9. Three possibilities for matching the LED spectrum to actual LED output are shown: (a) the closest single LED; (b) the closest combination of four types of LEDs operating under nominal conditions (with no spectral shift); and (c) the closest combination of four types of LEDs operating under nominal and overdrive conditions as described in the previous section. Qualitatively, this figure shows that the best match between desired and actual spectrum is achieved by the more flexible array (the one consisting of LEDs operating at nominal and overdrive conditions). The best matches (as measured by the error between desired and actual spectra) are configured as follows for each type of LED array as shown in Table 2.

The best, non-optimized, and single LED configurations are shown in Table 2 below.

TABLE 2

Configurations for GFPuv fluorophors

| Configuration | LEDs | Current |
|---|---|---|
| 5 LEDs at nominal operation | 1 blue | 10 mA |
|  | 1 blue | 10 mA |
|  | 1 blue | 20 mA |
|  | 1 blue-green | 10 mA |
|  | 1 blue-green | 20 mA |
| 5 LEDs in overdrive | 1 blue | 10 mA |
|  | 1 blue | 20 mA |
|  | 1 blue | 20 mA |
|  | 1 blue-green | 20 mA |
|  | 1 blue-green | 100 mA |
| Single LED | 1 blue | 50 mA |

Figure 11:
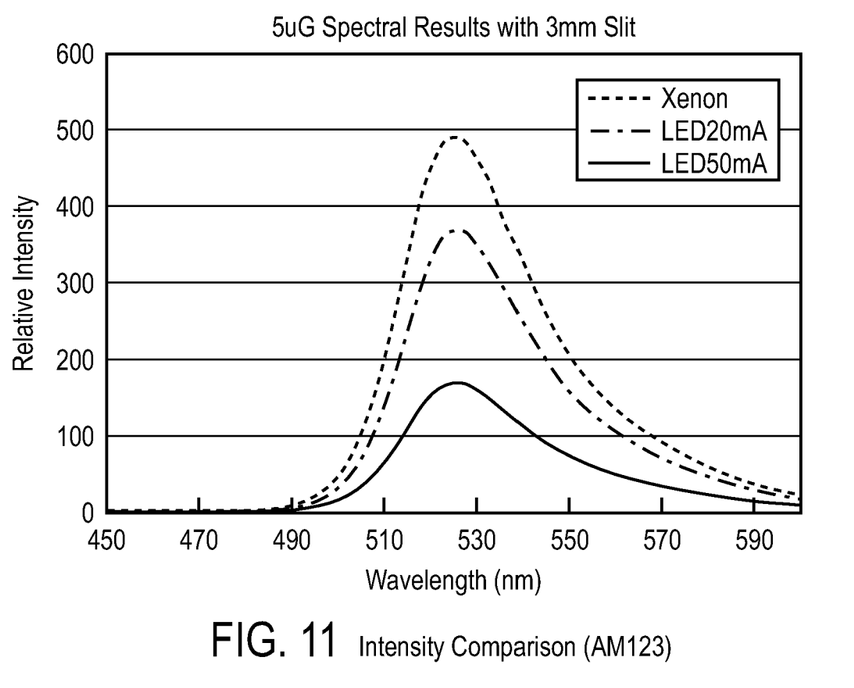
FIG. 11 is a graphical representation of an intensity comparison according to an embodiment of the present invention.

To complement these simulation results, the optimization process 600 and LED array 102 have been tested on two representative applications. The first application demonstrates that the LED array 102 is capable of producing an emission signal within 25% of the performance of the Xenon source for a biological analysis application (FIG. 11). The bacteria Methylobacterium extorquens AM123 is analyzed under identical experimental conditions for both the Xenon source and a five element LED array 102 consisting of purple LEDs operating at 20 mA (nominal operation) and purple LEDs operating at 50 mA (overdrive operation). While nominal operation does not enable the LEDs to approach the power output of the Xenon lamp, overdrive operation brings the LED generated emission output within 25% of that produced by the Xenon source.

Figure 10A:
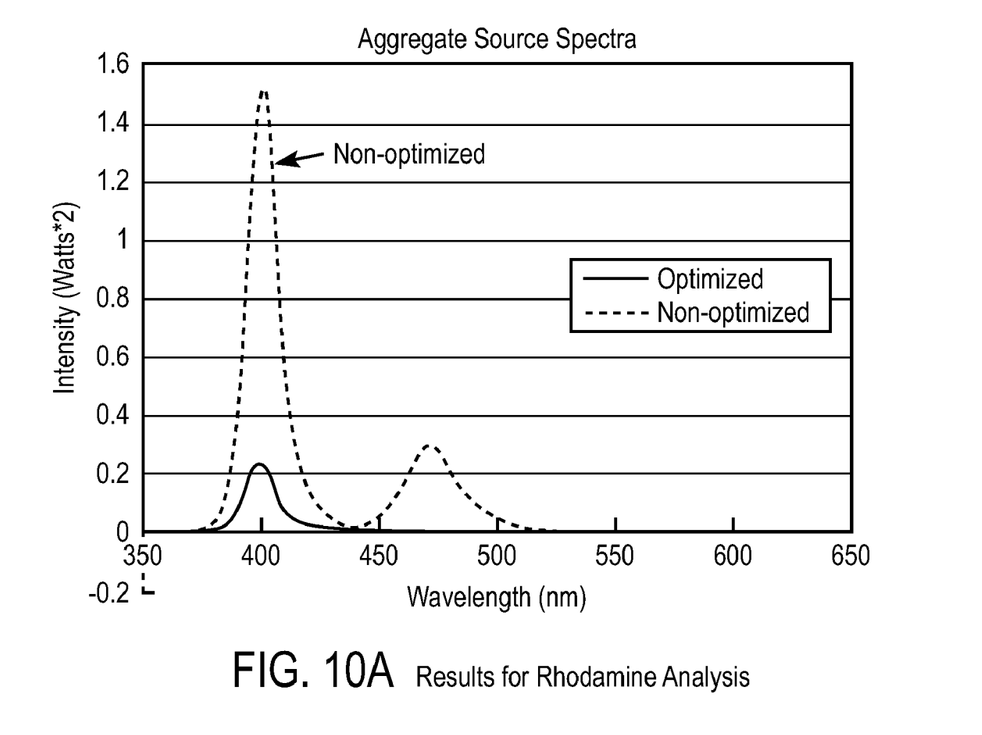
FIG. 10A and 10B are graphical representations of the results of Rhodamine analysis according to an embodiment of the present invention.
Figure 10B:
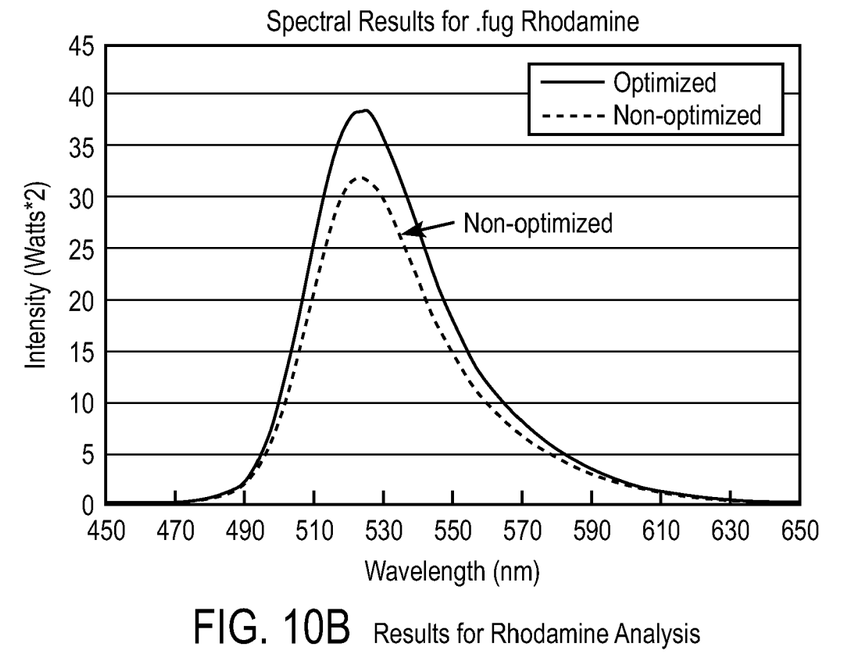

To demonstrate the increased efficiency of the LED array 102 presented here, the emission signal for the (a) single LED array and (b) optimized LED array is presented for the excitation of Rhodamine dye (FIG. 10). Despite the fact that the single LED array 102 (the closest match of a single LED excitation peak to the Rhodamine dye absorption characteristics) has a much greater intensity than the optimized LED array 102, the emission signal improves twofold over the non-optimized, single LED array 102. The optimized LED array 102 consists of two blue LEDs operating at 5 mA and three purple LEDs operating at 5 mA.

Embodiments of the present invention may be implemented using hardware, software, or a combination thereof. In implementations using software, the software may be stored on a machine-accessible medium. A machine-accessible medium includes any mechanism that may be adapted to store and/or transmit information in a form accessible by a machine (e.g., a computer, network device, personal digital assistant, manufacturing tool, any device with a set of one or more processors, etc.). For example, a machine-accessible medium includes recordable and non-recordable media (e.g., read only memory (ROM), random access memory (RAM), magnetic disk storage media, optical storage media, flash memory devices, etc.), as recess as electrical, optical, acoustic, or other form of propagated signals (e.g., carrier waves, infrared signals, digital signals, etc.).

In the above description, numerous specific details, such as, for example, particular processes, materials, devices, and so forth, are presented to provide a thorough understanding of embodiments of the invention. One skilled in the relevant art will recognize, however, that the embodiments of the present invention may be practiced without one or more of the specific details, or with other methods, components, etc. In other instances, structures or operations are not shown or described in detail to avoid obscuring the understanding of this description.

Reference throughout this specification to "one embodiment" or "an embodiment" means that a particular feature, structure, process, block, or characteristic described in connection with an embodiment is included in at least one embodiment of the present invention. Thus, the appearance of the phrases "in one embodiment" or "in an embodiment" in various places throughout this specification does not necessarily mean that the phrases all refer to the same embodiment. The particular features, structures, or characteristics may be combined in any suitable manner in one or more embodiments.

The terms used in the following claims should not be construed to limit embodiments of the invention to the specific embodiments disclosed in the specification and the claims. Rather, the scope of embodiments of the invention is to be determined entirely by the following claims, which are to be construed in accordance with established doctrines of claim interpretation.

What is claimed is:

1. An apparatus for performing fluorescence analysis using a plurality of drive currents, comprising:
   a light emitting diode (LED);
   control electronics to apply a plurality of drive currents to the LED, wherein a first drive current in the plurality of drive currents is to cause the LED to emit excitation light having a first color and/or first wavelength band, wherein a second drive current in the plurality of drive currents is to cause the LED to emit excitation light having a second color and/or second wavelength band, wherein at least one of the drive currents is greater than a nominal drive current for the LED;
   optics to couple the excitation light from the LED to a holder for a fluorophor, the fluorophor to emit light in response to the excitation light from the LED, the light emitted from the fluorophor having a color and/or wavelength band that is different from the color and/or wavelength band of the excitation light coupled to the holder;
   one or more photodetectors; and
   an optical signal path to couple the light from the holder to the photodetector.

2. The apparatus of claim 1, wherein at least one drive current has a variable duty cycle.

3. The apparatus of claim 1, wherein the control electronics are further to pulse at least one drive current to the LED.

4. The apparatus of claim 3, wherein the drive current is greater than a rated maximum current for the LED.

5. The apparatus of claim 3, wherein the control electronics comprise at least one active amplification circuit.

6. The apparatus of claim 1, wherein the first and second colors and the color emitted from the fluorophor are selected from at least one of blue, green, purple, and blue-green.

7. The apparatus of claim 1, wherein the optics to couple the excitation light from the LED to the holder for the fluorophor comprise an individual optical fiber bundle coupled to the LED, wherein the optical fiber bundle comprises a plurality of optical fibers.

8. The apparatus of claim 7, wherein the optical fiber bundle is bundled together to aggregate the excitation light from the LED into a single light beam having a substantially uniform intensity profile and/or a substantially uniform wavelength band distribution and to couple the single light beam to the holder for the fluorophor.

9. The apparatus of claim 8, wherein the plurality of optical fibers in the optical fiber bundle are bundled together in a random manner.

10. The apparatus of claim 8, further comprising a beam splitter to split off a small portion of the single light beam.

11. The apparatus of claim 10, further comprising high gain, low noise circuitry to measure the intensity of the small portion of the single light beam as a function of drive current.

12. The apparatus of claim 11, further comprising circuitry to adjust drive current to the LED in response to the measured intensity of the small portion of the single light beam, the circuitry comprising a feedback loop.

13. The apparatus of claim 11, wherein the circuitry to measure the intensity of the small portion of the single light beam as a function of the drive current comprises a spectrophotometer or spectrometer.

14. The apparatus of claim 8, further comprising at least one individual PIN diode coupled to the LED to detect excitation light emitted from the LED.

15. The apparatus of claim 14, further comprising circuitry to adjust at least one individual drive current to the LED in response to the detected excitation light emitted from the LED.

16. The apparatus of claim 1, wherein the holder for the fluorophor is a cuvette.

17. The apparatus of claim 1, wherein the photodetector is selected from at least one of a photomultiplier tube, an avalanche photodiode, photodiode, phototransistor, and a charge-coupled device (CCD).

18. A method for performing fluorescence analysis using a plurality of drive currents, comprising:
   receiving a first drive current in the plurality of drive currents at a light emitting diode (LED);
   emitting excitation light having a first color and/or first wavelength band in response to the first drive current;
   receiving a second or more drive current in the plurality of drive currents at the LED;
   emitting excitation light having a second color and/or second wavelength band in response to the second drive current, wherein at least one of the drive currents is greater than a nominal drive current for the LED;
   coupling the excitation light from the LED to a sample having a fluorophor therein;
   emitting light from the fluorophor in response to the excitation light, the light emitted from the fluorophor having a color and/or wavelength band that is different from the color and/or wavelength band of the excitation light coupled to the holder, the light emitted from the fluorophor also being different from the emitted light using first drive current and the second or more drive current; and
   coupling the light from emitted from the fluorophor to one or more photodetectors, the photodetectors having a spectral sensitivity to capture differences in color or wavelength band between emissions corresponding to the first drive current and the second or more drive currents.

19. The method of claim 18, further comprising varying the duty cycle of the first drive current.

20. The method of claim 18, further comprising varying the duty cycle of the second drive current.

21. The method of claim 18, further comprising measuring an intensity of a portion of the excitation light.

22. The method of claim 21, further comprising using feedback to adjust the first and/or the second drive currents in response to measuring the intensity of the portion of the excitation light.

23. A method for performing fluorescence analysis, comprising:
   receiving a first drive current at a light emitting diode (LED);
   emitting excitation light having a first color and/or first wavelength band in response to the first drive current;
   receiving a second drive current at the LED; and
   emitting excitation light having a second color and/or second wavelength band in response to the second drive current, wherein at least one of the drive currents is greater than a nominal drive current for the LED
   detecting the excitation light emitted from the LED;
   coupling the excitation light from the LED to a holder for a fluorophor;
   emitting light from the excitation light, the light emitted from the fluorophor having a color and/or wavelength band that is different from the color and/or wavelength band of the excitation light coupled to the holder; and
   coupling the light emitted from the fluorophor to a photodetector.

* * * * *

UNITED STATES PATENT AND TRADEMARK OFFICE
CERTIFICATE OF CORRECTION

| | | |
|---|---|---|
| PATENT NO. | : 7,583,381 B2 | Page 1 of 1 |
| APPLICATION NO. | : 12/107718 | |
| DATED | : September 1, 2009 | |
| INVENTOR(S) | : Wilson et al. | |

It is certified that error appears in the above-identified patent and that said Letters Patent is hereby corrected as shown below:

Column 14, line 30 (claim 23, Line 7) delete "and".

Column 14, line 38 (Claim 23, Line 15) after the phrase emitting light from, add -- the fluorophor in response to --.

Signed and Sealed this

Twelfth Day of October, 2010

David J. Kappos
*Director of the United States Patent and Trademark Office*